US009611500B2

(12) United States Patent
Cook et al.

(10) Patent No.: US 9,611,500 B2
(45) Date of Patent: Apr. 4, 2017

(54) METHOD FOR DETECTING THE PRESENCE OF THE VIABLE CELLS IN AN ENDODONTIC SAMPLE

(75) Inventors: Richard Cook, London (GB); Garrit Koller, London (GB); Timothy Watson, London (GB); Federico Foschi, London (GB); Francesco Mannocci, London (GB); Frederic Festy, London (GB)

(73) Assignee: KINGS COLLEGE LONDON, London (GB)

( * ) Notice: Subject to any disclaimer, the term of this patent is extended or adjusted under 35 U.S.C. 154(b) by 0 days.

(21) Appl. No.: 14/238,967

(22) PCT Filed: Aug. 14, 2012

(86) PCT No.: PCT/EP2012/065873
§ 371 (c)(1),
(2), (4) Date: Jul. 1, 2014

(87) PCT Pub. No.: WO2013/024088
PCT Pub. Date: Feb. 21, 2013

(65) Prior Publication Data
US 2014/0308694 A1    Oct. 16, 2014

(30) Foreign Application Priority Data

Aug. 17, 2011 (GB) .................................. 1114117.3

(51) Int. Cl.
| | | |
|---|---|---|
| C12Q 1/04 | (2006.01) | |
| A61B 1/24 | (2006.01) | |
| A61B 1/04 | (2006.01) | |
| C12Q 1/37 | (2006.01) | |
| A61B 1/06 | (2006.01) | |
| A61B 1/00 | (2006.01) | |

(52) U.S. Cl.
CPC .............. *C12Q 1/04* (2013.01); *A61B 1/043* (2013.01); *A61B 1/0684* (2013.01); *A61B 1/24* (2013.01); *C12Q 1/37* (2013.01); *A61B 1/00165* (2013.01); *A61B 1/0638* (2013.01)

(58) Field of Classification Search
None
See application file for complete search history.

(56) References Cited

U.S. PATENT DOCUMENTS

2011/0039226 A1*  2/2011  Armanino ..................... 433/32
2012/0028222 A1*  2/2012  Abdennour et al. .......... 433/224

FOREIGN PATENT DOCUMENTS

| WO | 95/08962 A1 | 4/1995 |
|---|---|---|
| WO | 2005/102033 A2 | 11/2005 |

OTHER PUBLICATIONS

Siegel J. et al. Studying Biological Tissue with Fluorescence Lifetime Imaging. Applied Optics 42(16)2995-3004, Jun. 1, 2003.*
Tan K. et al. Rapid Method for the Detection of Root Canal Bacteria in Endodontic Therapy. Journal of Endodontics 41(4)447-450, Apr. 2015.*
Wong, F., et al., "Axonal and Neuromuscular Synaptic Phenotypes in Wld<S>, SOD1<G93A> and Ostes Mutant Mice Identified by Fiber-Optic Confocal Microendoscopy," Molecular and Cellular Neurosciences, vol. 42, No. 4, Nov. 1, 2009, pp. 296-307.
Delgado, R.J.R., et al., "Antimicrobial Effects of Calcium Hydroxide and Chlorhexidine on Enterococcus Faecalis," Journal of Endodontics, vol. 36, No. 8, Aug. 1, 2010, pp. 1389-1393.
Pini R., et al., "Laser Dentistry: Root Canal Diagnostic Technique Based on Ultraviolet-Induced Fluorescence Spectroscopy," Lasers in Surgery and Medicine, vol. 9, No. 4, Jan. 1, 1989, pp. 358-361.
Ho, Quan V., et al., "Laser Fluorescence Assessment of the Root Canal Using Plain and Conical Optical Fibers," Journal of Endodontics, vol. 36, No. 1, Jan. 1, 2010, pp. 119-122.
Moshonov, Joshua et al., "Endoscopic Root Canal Treatment," Quintessence International, vol. 40, No. 9, Oct. 1, 2009, pp. 739-744.
Sarkissian, Ani et al., "Fiber Optic Fluorescence Microprobe for Endodontic Diagnosis," Journal of Dental Education, vol. 69, No. 6, Jun. 1, 2005, pp. 633-638.
Sainsbury, Andrew L. et al., "DIAGNOdent Laser Fluorescence Assessment of Endodontic Infection," Journal of Endodontics, vol. 35, No. 10, Oct. 1, 2009, pp. 1404-1407.
Siegel, Jan., et al., "Studying Biological Tissue with Fluorescence Lifetime Imaging: Microscopy, Endoscopy, and Complex Decay Profiles," Applied Optics, Optical Society of America, vol. 42, No. 16, Jun. 1, 2003, pp. 2995-3004.

* cited by examiner

*Primary Examiner* — Ralph Gitomer
(74) *Attorney, Agent, or Firm* — The Marbury Law Group, PLLC

(57) ABSTRACT

A method and apparatus for detecting the presence of the viable cells in an endodontic sample in or taken from an endodontic cavity in the tooth, such as the root canal, enables the rapid and low cost identification of the presence or absence of bacteria or other viable cell tissue in the endodontic space by first incubating a viable cell indicator with an endodontic sample for a pre-determined period suitable for chair-side test and then measuring and/or detecting a change in a parameter (e.g. fluorescence) associated with the viable cell indicator. Thereby, the required level of root canal treatment can be reached which minimizes the risk of re-infection without the time, cost and potentially harm of over-preparation and over treatment by the dental surgeon or of a re-treatment.

15 Claims, 4 Drawing Sheets

(a)            (b)            (c)

METHOD FOR DETECTING THE PRESENCE OF THE VIABLE CELLS IN AN ENDODONTIC SAMPLE

CROSS REFERENCE TO RELATED APPLICATIONS

This is a national stage application of PCT/EP2012/065873, filed internationally on Aug. 14, 2012, which claims priority to Great Britain Application No. 11141173, filed on Aug. 17, 2011, both of which are incorporated herein by reference in their entireties.

FIELD OF THE INVENTION

This invention pertains generally to the field of endodontic imaging. More particularly, the invention relates to a method and apparatus for imaging, quantitative measurement and/or data collection inside a tooth, and more particularly the root canal.

BACKGROUND OF THE INVENTION

Endodontic therapy or root canal treatment is the treatment of choice for prevention or recovery of a tooth from infection, or where it is otherwise threatened by infection, cracking or decay, extending (into or near) to or approximating the pulp chamber.

Bacterial infection in the root canal or tooth, typically affecting the pulp material, causes a process of pulpitis, an often painful process affecting the pulp chamber or endodontic chamber and root canal structure. This results in an infection of the tooth and often results in an extending lesion beyond the apex or other canal connecting the nerve space to the adjacent soft and hard tissues of a tooth and may present as an abscess within these surrounding tissues. Infected and inflammatory bacterial fluids emanating from within the tooth structure and apical portion of the tooth escape through the apex of the root into the surrounding periodontal tissue, causing substantial inflammation, with associated tissue changes. Without intervention, the tooth will die and may require extraction and the infection may spread into the surrounding tissues causing potentially life-threatening abscesses in the head and neck region. Root canal treatment (endodontic therapy) allows treatment of such infection and the structural integrity of the tooth to be saved.

The purpose of root canal treatment is to entirely remove all tooth pulp and living tissue as well as any bacterial organism or biofilm and to seal off the root canal by filling the pulp cavity. This allows the crown portion of the tooth to be restored safely using established restorative options such as composite filing or artificial crowns, thereby retaining a non-vital tooth in structural and functional senses.

A typical procedure that dentists will undertake in a root canal treatment on a patient is to open the tooth by drilling through the crown, removal of the pulp (which comprises blood vessels, nerve tissue and soft tissue and which is typically infected in a tooth undergoing root canal treatment), cleaning and enlarging of the root canal (e.g. with an incremental series of small files) to ensure that all infected material is removed and to ensure that the root canal is large enough to be effectively filled. Where there are multiple roots, each will have to be identified, cleaned and treated. Furthermore, roots may have a complex morphology in terms of overall structure including curvature and accessory canals. Typically, removal of pulp material and enlarging of the root canals will be done at a first visit. An antibacterial (e.g. sodium hypochlorite) will typically be applied into the endodontic cavity to enhance the removal and killing of any residual microbial burden. Optionally the tooth will be temporarily filled and closed and reopened at a second visit at which point, cleaning of the endodontic cavity will be resumed. A root canal filling material will be inserted into the cavity and a well-fitted filling, such as a glass ionomer cement, and, optionally, a crown will seal the tooth and ideally prevent re-infection.

The most common cause of failure of root canal treatment, aside from poor technique (e.g. missed root canal or improperly sealed access cavity) or iatrogenic contamination, is residual bacteria in the root canal space and at the apex of the tooth, which can arise due to difficulty in visualising or accessing all aspects of the inside of the roots, particularly in the apical region, of the root canal which may harbour remaining tissue or bacteria. As a result, dental practitioners may over-prepare the canals to remove the infected dentine, at potentially unnecessary time and cost, or may underprepare leaving a substantial bio-burden within the tooth structure with concomitant risk of re-infection. In England and Wales alone, over 1,000,000 RCTs (root canal treatments) were carried out in NHS surgery in 2003 (Dental Practice Board, 2003). Yet, still, approximately 15-25% of endodontic root canal procedures fail. Therefore, these procedures often need to be repeated due to persistent infection, thus representing a significant time and cost burden, in addition to often requiring specialist intervention and dramatically reducing the prognosis of the tooth to be treated. Since it has been proven that the complete disinfection of the root canal space improves the chances of favourable outcome (80% vs 44%) of the root canal treatment, microbiological sampling of the canal content could be sued to determine the bacterial content. However, this procedure is inherently flawed as it adds several days to the procedure time (since microbial analysis in a cell culture laboratory is required) and furthermore, bacteria cultures will only identify bacteria present in the obtained sample as well as being limited to culturable material and so can result in false negatives. This leads to canals which ultimately fail as they are still infected at the time of obturation despite negative culture results.

A number of patent publications exist in the field of endodontics, bacteria eradication and imaging.

WO-A-2005/102033 describes a method of radiation ablation of residual bacterial and biofilm populations in a root canal, typically the apical portion of the root canal, which is difficult to reach with instruments and irrigation fluid. An optical probe with a head that causes lateral dispersion of the near infra-red radiation enables thermolytic eradication of bacteria and biofilm without the problems of hot-tip and other such problems experienced with previous laser ablatement methods. However, the apparatus is expensive and only effective in and insofar as the probe is inserted into the appropriate root canals. Furthermore, this device will not assess the actual presence of viable bacteria pre- or post-treatment.

WO-A-95/08962 describes a method of imaging a root canal utilising induced fluorescence imaging or induced fluorescence spectroscopy. In undertaking an endodontic treatment, dentists may obtain X-ray images of the tooth in order to establish the structure and in particular the number and shape of roots (and root canals) in the tooth. A problem with X-ray is that the apical portion of the root canal (the portion where structural complexities are likely to exist) is partially obscured in such images by the jaw bone. An apparatus comprises an elongated tool and optical fibre which carries ultraviolet and blue light to induce fluorescence within the root canal. Fluorescence is captured by the optical fibre and transmitted to a sensor which monitors return light to build an image of the root canal structure. There is no disclosure of determining the presence or absence of bacteria using the probe and further, the probe and sensor is a complex kit as is necessary to deliver sufficient radiation to excite and detect fluorescence.

There is a need for a chair-side test to determine the presence of biofilm, bacterial cells or other cells or cell debris in the endodontic space during endodontic therapy.

The present inventors have devised a method and instrument for the identification of cells, and particularly viable cells, and a method for achieving and identifying a preparation-phase treatment endpoint for use in situ in the dental clinic during endodontic therapy.

Problem to be Solved by the Invention

There remains a need for improvements in endodontic therapy.

It is an object of this invention to provide an apparatus for and method of identifying the presence of cells, especially viable cells, in endodontic material/fluid/tissue or in the endodontic cavity.

It is a further object of the invention to provide a substance or substances for the above object.

It is a still further object of the invention to provide an apparatus and method for use in the assessment of the presence of viable bacterial in the root canal and diagnosis and treatment of endodontic bacterial infection

SUMMARY OF THE INVENTION

According to a first aspect of the invention, there is provided a method of detecting the presence of cells or cellular material, especially viable cells or viable cell material, in an endodontic sample, the method comprising the steps of: incubating a cell indicator (preferably a viable cell indicator) with an endodontic sample for a pre-determined period; and measuring and/or detecting a change in a parameter (or set of parameters) associated with the cell indicator (or viable cell indicator) to obtain an indication result; whereby an indication result representing a pre-determined change in the parameter is indicative of cells or cellular material (especially viable cells or viable cell material) in the sample.

In a second aspect of the invention, there is provided a cell indicator (especially a viable cell indicator) for use in the diagnosis, prophylaxis and/or treatment of endodontic infection or recurrence of endodontic infection.

Advantages of the Invention

By utilizing the indicators, e.g. fluorescent dyes, described in the apparatus and methods of the invention, the presence or absence of bacteria and other cell tissue or viable or non-viable cells (especially viable cells) in the endodontic space or in endodontic fluid, which presence is the primary reason for root canal treatment failure, may be identified by low-cost, rapid and readily available means. Thereby, the required level of treatment can be reached which minimizes the risk of re-infection without the time, cost and potentially harm of over-preparation and over treatment by the dental surgeon or of a re-treatment to be carried out by a specialist.

DETAILED DESCRIPTION OF THE INVENTION

Figure 1:
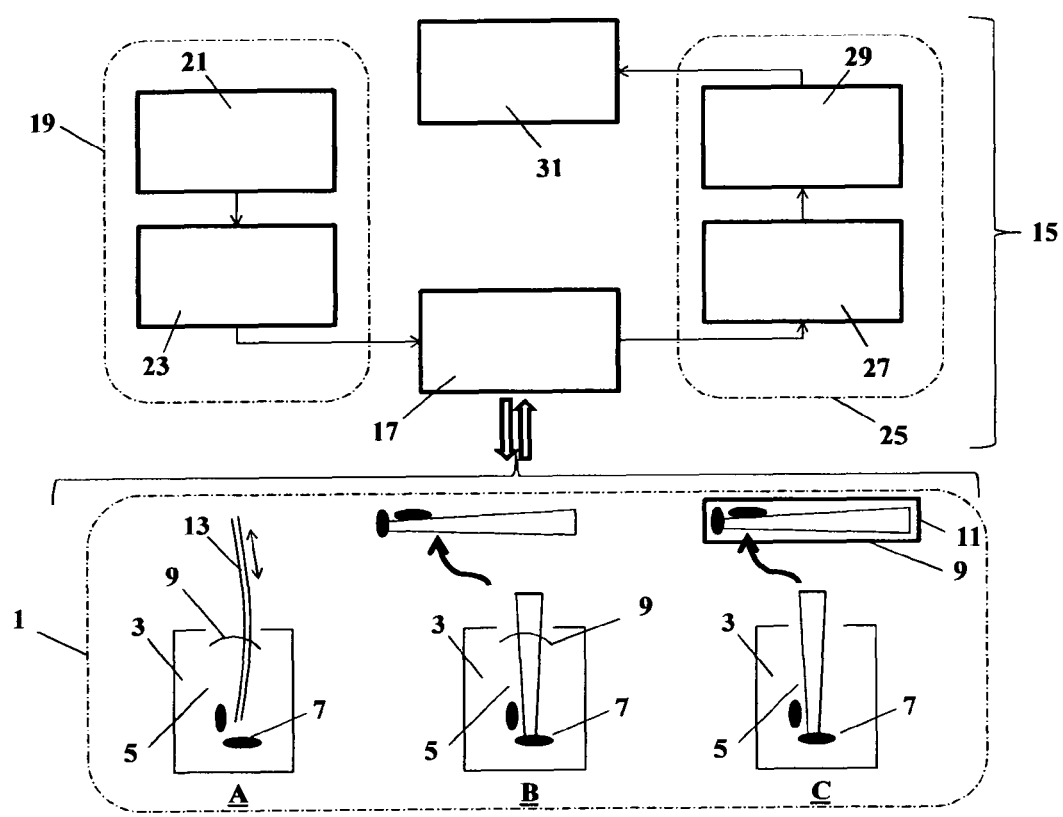
FIG. 1 is a flow chart which illustrates schematically implementation of an embodiment of the invention according to three methods of implementation.

The invention provides for improved methods, apparatus and compositions for detecting the presence of cells, live or dead, or cellular material (including extracellular material), but especially of bacteria or other viable cells or viable cell material, in an endodontic fluid or endodontic cavity, which may be useful as an ex vivo chair-side test and/or in the (preventative) diagnosis, prevention or treatment of dental abscess, dental abscess recurrence or endodontic therapy. Such chair-side test may be useful in rapidly evaluating the presence and, optionally, persistence of cellular content (especially viable cellular content) in the root canal, e.g. at the end of root canal treatment.

The method of the present invention preferably comprises the detecting of the presence of or viability of viable cells or viable cell material in an endodontic sample. The detection of viable cells and/or measurement of quantity, population or type of viable cells in an endodontic sample may be useful for a number of purposes, including identifying the need for (further) cleaning during endodontic treatment, determining the treatment end-point during an endodontic treatment process, identifying presence and optionally persistence of infection in an endodontic cavity and identifying the type of infection in an endodontic cavity. The methods (and apparatus and compositions) of the invention find particular utility in identifying the therapeutic end point during cleansing of the endodontic cavity during endodontic therapy whereby the point at which all live cellular matter is eliminated can be identified such that risk of re-infection is minimized. The methods of the invention comprise the steps of incubating a viable cell indicator with an endodontic sample (typically, for a pre-determined period); and measuring and/or detecting a change in a parameter associated with the viable cell indicator to obtain an indication result, whereby an indication result representing a change (typically a pre-determined change) in the parameter is indicative of viable cells or viable cell material in the sample.

There are three main embodiments of the method of the invention, which are discussed in more detail below.

In a first main embodiment, the incubating step of the method is conducted within the endodontic cavity by applying a viable cell indicator or component thereof to the endodontic cavity and the measuring and/or detecting step is conducted in the endodontic cavity.

In a second main embodiment, the incubating step is conducted within the endodontic cavity by applying a viable cell indicator or component thereof to the endodontic cavity and the measuring and/or detecting step is conducted ex vivo, i.e. outside the body and outside of the endodontic cavity.

In a third main embodiment, the incubating step is conducted ex vivo by incubating the viable cell indicator or component thereof with an endodontic sample taken from the endodontic cavity and the measuring and/or detecting step is conducted ex vivo.

The term 'endodontic therapy' as used herein is akin to the process, or parts of the process, involving root canal treatment. Typically, endodontic therapy comprises the treatment of a tooth which is identified as having an infection therein by excavating the tooth (of pulp and live matter), cleansing the tooth to eradicate any bacterial or host viable cell matter (for preventing re-infection), closing any apical apertures, e.g. via obturation of the canal, and filling the tooth (optionally providing coronal restoration of the tooth) such as to preserve the tooth.

An 'endodontic fluid' or 'endodontic sample', as used herein, is a fluid or sample in or taken from an endodontic cavity and comprising matter from within the tooth (be that cellular matter or infectious or inflammatory matter) or endodontic cavity.

An 'endodontic cavity' as used herein is a cavity existing or formed within a tooth during endodontic therapy. Typically, an endodontic cavity is formed (or enlarged) by drilling a hole in the crown of the tooth, removing pulp matter, nerve matter and blood vessels and bacteria from the tooth to form a cavity bound by dentine. The endodontic cavity will typically comprise several portions, including a crown portion and in each root an apical portion being the third of the root closest to the apex of the root.

As used herein, a 'viable cell' means a cell that is alive and/or is capable of reproducing and/or is capable of producing a function. Typically, a viable cell may be a eukaryotic or prokaryotic cell, which eukaryotic cells are primarily host cells. 'Viable cell material' includes structures or compounds associated or derived from viable cells, e.g. extracellular such structures or compounds, such as constituent polysaccharides and enzymes within a biofilm structure (e.g. a viable biofilm).

The methods of the invention require the incubation of a viable cell indicator with an endodontic sample, which viable cell indicator has associated with it a parameter (an indication parameter) capable of exhibiting a detectable and/or measurable change in the presence of a viable cell or viable cell population. Such measurable or detectable change in a parameter may be such that measurement and/or detection thereof represents an indication result (which may be, for example, presence or absence of viable cells, presence or absence at pre-determined threshold of viable cells, risk factor of presence of viable cells, population or concentration of viable cell population, presence and optionally type of viable cells). Preferably an indication result is a binary result, representing either presence of viable cells (or presence of viable cells in a population above a pre-determined detection threshold) or absence of viable cells (or presence of viable cells below a pre-determined detection threshold).

The indication parameter, or property, of the indicator may be any suitable parameter for which, for example, there is a detectable and/or measurable change when the indicator is incubated in an endodontic sample in the presence as compared with absence of viable cells. The indication parameter may be, for example, temperature (represented by a thermal change), pH (represented by a change in pH), conductivity (represented by a change in conductivity), enzymatic activity (e.g. protease activity) or spectrophotometric wavelength (e.g. represented by presence or absence of certain absorption emission wavelengths).

Preferably, however, the indicator is luminescence mediated and the parameter or property associated with the indicator is luminescence or certain luminescent behaviour (e.g. wavelength of luminescence). Luminescence may be, for example, photoluminescence (e.g. fluorescence or phosphorescence), chemiluminescence, bioluminescence, electroluminescence or mechanoluminescence.

Where particular embodiments are discussed herein with respect to a particular type of cell indicator, where the context allows the cell indicator may not necessarily be limited to that mentioned and may be substituted by another type of viable cell indicator as described herein.

The indicator, in order to provide the effect of indicating described above (whereby detection and/or measurement of a parameter associated with the indicator may result in an indication result), preferably comprises a first form in the absence of viable cells (or associated viable cell matter) in which it exhibits a first parameter behaviour and a second form in the presence of viable cells (or associated viable cell matter) in which it exhibits a second parameter behaviour. The first and second parameter behaviours are measurably or detectably distinct, e.g. a measurable increase in temperature (where temperature is the indicator parameter), a measurable or detectable change in pH (where pH is the indicator parameter), a measurable or detectable change in conductivity (where conductivity is the indicator parameter), a measurable or detectable change in enzymatic activity or population or form (e.g. where the indication parameter is presence of an enzyme, e.g. extracellular enzyme, implicated in a viable cell activity), a measurable or detectable change in spectrophotometric properties or, in particular, a measurable or detectable change in luminescence.

The indicator may comprise a single component capable of interaction with a viable cell (or signal or molecule associated with a viable cell) and of exhibiting first and second parameter behaviours in order to produce an indication result or may comprise two or more components which together are capable of interaction with a viable cell (or signal or molecule associated with a viable cell) and of exhibiting first and second parameter behaviours. For example, in the latter case, an indicator may comprise: a first component which is capable of interacting with a viable cell, which first component has a dormant form, preferably in the absence of viable cells, and an active form, preferably in the presence of viable cells; and a second component capable of exhibiting the indication parameter and/or change in indication parameter, which second component has a first form in which it has a first parameter behaviour and a second form in which it has a second parameter behaviour, the second component being caused to adopt its second form and exhibit its second parameter behaviour in the presence of the activated form of the first component, thereby a change in parameter behaviour may be exhibited by the presence of viable cells. Preferably, however, a single component of the indicator is capable of interacting with viable cells (e.g. is substrate for viable cells or a viable cell component), and preferably having dormant (in the absence of viable cells) and activated (in the presence of active cells) forms, and is capable of exhibiting first and second parameter behaviours associated with the dormant and active forms (e.g. exhibits distinct parameter behaviours associated with the presence and absence of viable cells).

Optionally, where an indicator comprises two or more components, a first component may be used in vivo, for example in an endodontic cavity, in which it may be incubated in an endodontic sample (and in the presence of viable cells form an activated form of the first component) and a second component may be used either in vivo at the same time or added later, or ex vivo, by sampling the incubated sample and incubating the incubated sample with the second component, whereupon presence of the activated first component may cause a change in the indicator parameter as exhibited by the second component. This may be a useful embodiment where the first component is suitable for use in the endodontic cavity but the second component is not suitable for use in or on a patient. Preferably, however, as mentioned above, the indicator comprises a single component capable of both interacting with viable cells and exhibiting a parameter associated with their presence/absence.

An indicator or component thereof may interact with a viable cell, for example, by reaction or interaction with cell surface receptors, by enzyme-catalysed reaction, by forming complexes (e.g. by intercalation) with DNA (e.g. prokaryotic DNA) or with cell proteins or by accumulation within living cells, which interactions may be capable of distinguishing living cells.

Preferably, as mentioned above, the indicator is luminescence mediated. An indication result may be represented by quenching of a certain luminescent behaviour (e.g. luminescence, intensity of luminescence above a pre-determined threshold or a certain distinct wavelength of luminescence) by the presence of viable cells in an endodontic sample or, preferably, by activation of a certain luminescent behaviour (e.g. luminescence, intensity of luminescence above a predetermined threshold or a certain distinct wavelength of luminescence) by the presence of viable cells.

Preferably, therefore, the indicator as used in the methods of the invention is or comprises a luminescent component which has a first form which exhibits a first luminescent behaviour (e.g. no luminescence, luminescence below a certain or pre-determined threshold intensity and/or luminescence at a distinct wavelength) in the absence of viable cells and a second form which exhibits a second luminescent behaviour (e.g. luminescence, luminescence above a certain or predetermined threshold intensity and/or luminescence at a distinct wavelength).

The first and second forms may represent a chemical reaction (e.g. removal of a protecting group) in the presence of viable cells or a component thereof, or may represent the transition between two conformational forms as between the presence and absence of viable cells or a component thereof.

The indicator may be phosphorescence-mediated (that is, the indicator should be capable of exhibiting a distinct detectable and/or measurable phosphorescence or change in phosphorescence in the presence/absence of viable cells), or preferably fluorescence-mediated (that is, the indicator should be capable of exhibiting a distinct detectable and/or measurable fluorescence or change in fluorescence in the presence/absence of viable cells).

Optionally, the indicator may be chemiluminescent, by which it is meant that the indicator may exhibit luminescence resulting from a chemical reaction.

Preferably, as mentioned above, the indicator is photoluminescence mediated and more preferably fluorescence mediated. Accordingly, the indicator preferably has a first form in which the indicator has a first fluorescent behaviour (e.g. no fluorescence, fluorescence below a pre-determined threshold intensity or fluorescence at a particular wavelength) and a second form in which the indicator has a second fluorescence behaviour (e.g. fluorescence, fluorescence above a pre-determined threshold intensity or fluorescence at a particular wavelength). Preferably, the fluorescence-mediated indicator indicates the presence or absence of viable cells by having fluorescent and non-fluorescent forms. Optionally, the presence of viable cells may quench fluorescence in the indicator but preferably the presence of viable cells or components thereof activate fluorescence in the indicator.

Optionally the indicator may adapt its conformation between first (non-fluorescent) and second (fluorescent) forms according to the absence and presence respectively of viable cell populations in the sample in which it is incubated. This has a potential benefit, e.g. if used in situ, that a composition for killing viable cells may be added and the indicator may show the population depleting or reaching its desired zero population end point. However, preferably, the transition of the indicator in its first form (non-fluorescent) in the absence of viable cells to its second form (fluorescent) in the presence of viable cells is a single occasion transition. Thus, the presence of viable cells in a sample may be recorded without risk of losing that record and thereby risking a false negative result.

Preferably the luminescence mediated indicator is a single component or dye capable of transitioning from its first (e.g. dormant or non-fluorescent) form to its second (e.g. active or fluorescent) form in the presence of viable cells or a component thereof.

The indicator (or dye, which for indicators that include components capable of emitting visible spectrum or UV or IR light may be used interchangeably with indicator) may interact with viable cells or components thereof in order to convert from its first form to its second form by any suitable means which enables it to distinguish viable cells from non-viable cells, such as for example by viable cell enzyme mediated reaction (e.g. where the indicator may be Calcein-AM in its first, dormant form, or FRET peptides such as 5FAM-GPLGP peptides and tetrazolium dyes), viable cell DNA or protein complexing action, DNA intercalating action (e.g. where the indicator may be DAPI, Hoechst 33258) and/or by the effect of accumulating inside living cells (whereby the effect may be by increased intensity of signal).

Most preferably, when used in vivo (e.g. the sample is incubated in the endodontic cavity), the indicator is preferably biocompatible and more preferably is a vital dye, by which it is meant that the dye or indicator itself does not cause cell death.

In a preferred embodiment, the indicator comprises a live-cell targeting fluorophore and may preferably be selected from one or a combination of the following indicators (which are referred to in either the active, i.e. fluorescent, second form or the inactive, i.e. non-fluorescent, first form): DAPI, EBFP, Hoechst 33258 dye, 7-hydroxy-4-methylcoumarin, Quinine Sulfate, 4-methylumbelliferone, 5-FAM, Calcein, DiO, Fluorescein, FLUO-3, FLUO-4, EGFP, GFP, Oregon Green 514, Rhodamine Green, SYBR Gold, SYBR Green, SYTO 9, SYTOX Green, YFP, LIVE/DEAD BacLight, Alexa Fluor 555, Cy3, Ethidium Bromide, Ethidium Homodimer-1, Propidium Iodide, Resorufin, RFP, Rhod-2, Rhodamine Red, SYTOX Orange, TAMRA, Texas Red, TRITC, Allophycocyanin, Cy5, DRAQ5, SYTOX Red, Indocyanine green, sodium fluorescein, carboxyfluorescein, methylene blue, or ProSense 750.

Where an active form of the indicator is mentioned above, it is to be understood that the indicator comprises an inactive probe form thereof convertible to the active form in the presence of viable cells. In many examples, such as Calcein as the active form indicator, the indicator will require a precursor form such as Calcein-AM or the active form may be quenched in a peptide, such as 5FAM-peptide-TAMRA (e.g. with a peptide length in the region of 20 amino acids), whereby viable cell enzyme mediated cleavage will release the active fluorophore thus indicating presence of viable cells.

Preferred examples of indicator (in active form) are indocyanine green, sodium fluorescein, carboxyfluorescein, calcein, methylene blue and ProSense 750.

In a particularly preferred embodiment, the indicator is calcein (and preferably in its first, non-fluorescent precursor form, calcein-AM).

In a further embodiment, the indicator is incubated in the endodontic sample for 15 minute or less, more preferably 10 minutes or less, still more preferably 5 minutes or less and most preferably for 2 minutes or less.

The indicator composition may be provided in any suitable form as appropriate to the particular embodiment of the method being adopted. For example, the indicator may be provided in pre-filled ampoules of indicator in a solute at a pre-determined concentration appropriate for direct addition to the endodontic sample or cavity, or as a concentrate solution for dilution immediately prior to use, or as a pre-loaded syringe, as a powder ready for solution with water or saline solution. In one embodiment, the indicator may be provided impregnated or embedded into a paper tip.

The indicator is preferably utilized in a solution at a concentration suitable for eliciting the desired indicating effect. For example, especially in the case of Calcein-AM as the indicator, the indicator may preferably be utilized in a concentration in the range from 10 nM to 10 mM. The volume of indicator solution that may be required, for example for incubating in the endodontic cavity, is preferably approximate to the volume of a root canal, preferably in the range 10 µl to 500 µl.

The detection step may be any step capable of detecting the desired parameter of the indicator. In the preferred embodiments of the invention in which the indicator is fluorescence mediated, the detection step is a fluorescence detection or measuring step and may be conducted using any suitable apparatus, such as a spectrometer (e.g. a fluorescence spectrometer, such as a confocal fluorescence spectrometer) or by fluorescent microendoscopy (in the case of in situ detection) such as confocal fluorescent microendoscopy.

In a further aspect of the invention, as discussed above, there is provided an apparatus for use in the method of the invention. The apparatus may be adapted appropriate for each of the three main embodiments of the method of the invention as will be discussed below.

The three main embodiments will now be discussed in more detail in a preferred form.

In the first main embodiment, the incubating step of the method is conducted within the endodontic cavity by applying a viable cell indicator or component thereof to the endodontic cavity and the measuring and/or detecting step is conducted in the endodontic cavity.

Preferably according to this embodiment, the viable cell indicator is luminescence mediated, more preferably fluorescence mediated and more preferably the viable cell indicator comprises a fluorescent dye which has a first form, in the absence of a viable cell population in which the dye is not fluorescent and a second form, in the presence of a viable cell population in which the dye is fluorescent. The transition from the first form to a second form is preferably by way of cleavage of a moiety from the first form of the dye which cleavage is preferably catalysed by a viable cell enzyme.

The indicator preferably comprises one or more fluorescent dye, such as those listed above, but is more preferably a vital dye. Most preferably the indicator is selected from one or more of indocyanine green, sodium fluorescein, carboxyfluorescein, calcein, methylene blue and ProSense 750. In a particularly preferred embodiment, the indicator is calcein (and preferably in its first, non-fluorescent precursor form, calcein-AM).

Preferably the incubating step comprises applying the indicator into the endodontic cavity in the form of a solution, preferably an aqueous solution (e.g. a saline solution). The indicator should then be incubated for a predetermined period, which is preferably 15 minute or less, more preferably 10 minutes or less, still more preferably 5 minutes or less and most preferably for 2 minutes or less.

The incubating step preferably comprises administering a volume of indicator solution that will occupy the endodontic cavity and so in a volume of, for example, from 0.1 µl to 2 ml, preferably 500 µl to 2 ml.

A detection step according to this main embodiment preferably comprising inserting a detection probe, configured to detect an indication parameter or to transmit an indication parameter, e.g. fluorescence, associated with the indicator, into the incubating sample within the endodontic cavity. Preferably, the detection probe is inserted into each of the root cavities of the endodontic cavity. In a preferred embodiment, the detection probe is a fibre optic device connected or coupled to an external spectrometer or a photo-detector with an appropriate optical filter.

An apparatus according to one embodiment for use with a first main embodiment of the method of the invention comprises a detection probe, which is preferably a fibre optic core, coupled with a detection unit which is configured to detect the indicator parameter to produce an indication result (or data from which an indication result can be determined) and to display, communicate or transmit the data or indication result.

In a preferred embodiment, in which the method utilizes a luminescence-mediated, preferably fluorescence mediated, dye indicator, the apparatus comprises a detection probe, preferably a fibre optic core, and a detection unit as described above. The detection unit is preferably configured for coupling with a fibre optic (single or multi-use) and comprises an emission source for providing an excitation signal for (i.e. at a wavelength of absorption of) the active form of the dye. The emission source may be, for example, a monochromatic source such as a laser or a narrowband source such as LED. Preferably, for an indicator such as Calcein AM, the emission source is configured to emit at 485-500 nm more preferably ~488 nm. The detection unit should also be configured to detect light at a wavelength of emission from the dye indicator utilized, and may comprise, for example a photocell or spectrometric device, typically picking up the light emitted after filtering excitation and subsequent emission wavelengths.

This apparatus for use in in situ detection, can inherently provide a single point measurement since the user has the ability to move the probe up and down to sample across or along the entire root canal wall. The detection probe is preferably a fibre optic core or optical fibre and preferably comprises a single core fibre. The size of (i.e. diameter) of the fibre optic core may be selected according to the minimum root canal diameter, but in any case is preferably in the range of from 50 μm to 700 μm and more preferably from 100 μm to 500 μm, e.g. about 200 to about 300 μm. Conventional single core fibres may be used. The fibre optic core may be of any suitable material. Optionally, the fibre optic core is of a plastic material and preferably a plastic selected for low autofluorescence within the detection range of the detection unit or within 100 nm of the emission wavelength of the indicator dye. Preferably glass fibre optic cores are used.

The detection probe, preferably comprising a fibre optic core, is of a length required to pass from the user's hand inserting the tip of the probe into the endodontic cavity of a patient's tooth to the detection unit and is typically 1 m in length or less, preferably 50 cm or less. Preferably, the entire apparatus is hand held and thus comprises the detector unit in close proximity, which may be held in one hand by the user whilst the other hand is used to manoeuvre the tip of the probe and thus the fibre optic core may be, for example, 50 cm or less or even 30 cm or less, perhaps 10 cm or less or, in the case of a very small detector unit which may be held in the same hand maneuvering the tip, 5 cm or less. The detection unit could be design also as a handpiece with a probe attached, with the detection unit directly integrated in the dental chair unit.

Preferably, the detection probe (or a portion thereof) may be separated from the apparatus and thus single use probes or probe tips may be utilized, thus allowing smaller less robust probe tips to be used (which provide better access to root canals and better imaging) and reducing the labour required in cleaning the tips for re-use.

Preferably, the emission source (which provides excitation light at approximately an absorbance maxima of the selected detector dye) comprises an LED source, e.g. coupled to a narrowband filter (which would avoid bleedthrough into the dichroic). The detector unit is typically provided with a dichroic filter to remove the excitation light prior to detection. The final detection step by the detection unit can be done by either a spectrometer or a photo-multiplier-tube or photocell-type detector or other suitable detector. For a single dye system, a photo-multiplier tube is the easiest and most cost effective way, but for a multi dye system, a low cost spectrometer will allow multiple signals to be detected.

In a second main embodiment, the incubating step is conducted within the endodontic cavity by applying a viable cell indicator or component thereof to the endodontic cavity and the measuring and/or detecting step is conducted ex vivo, i.e. outside the body and outside of the endodontic cavity.

Preferably according to this embodiment, the viable cell indicator is luminescence mediated, more preferably fluorescence mediated and more preferably the viable cell indicator comprises a fluorescent dye which has a first form, in the absence of a viable cell population in which the dye is not fluorescent and a second form, in the presence of a viable cell population in which the dye is fluorescent. The transition from the first form to a second form is preferably by way of cleavage of a moiety from the first form of the dye which cleavage is preferably catalysed by a viable cell enzyme.

The indicator preferably comprises one or more fluorescent dye, such as those listed above, but is more preferably a vital dye. Most preferably the indicator is selected from one or more of indocyanine green, sodium fluorescein, carboxyfluorescein, calcein, methylene blue and ProSense 750. In a particularly preferred embodiment, the indicator is calcein (and preferably in its first, non-fluorescent precursor form, calcein-AM).

Preferably the incubating step comprises applying the indicator into the endodontic cavity in the form of a solution, preferably an aqueous solution (e.g. a saline solution). The indicator should then be incubated for a predetermined period, which is preferably 15 minute or less, more preferably 10 minutes or less, still more preferably 5 minutes or less and most preferably for 2 minutes or less.

The incubating step preferably comprises administering a volume of indicator solution that will occupy the endodontic cavity and so in a volume of, for example, from 0.1 μl to 2 ml, preferably 500 μl to 2 ml.

The detection step according to this main embodiment is conducted ex vivo and thus certain limitations on the detection apparatus are removed as compared to the first main embodiment. Thus an endodontic sample may be removed from the endodontic cavity after an incubation period, by for example a sampling step, prior to detection. The sampling step may comprise drawing a sample of the incubating fluid from the endodontic cavity using a syringe or other fluid sampler. It may then be applied to a detection element, which may be, for example, a plate (e.g. microplate), cuvette or the like, where the detection step may take place. Preferably, the sampling step comprises absorbing fluid from the incubating sample of the endodontic cavity into a paper point immersed therein. Paper points are commonly used in dental endodontic treatment. Preferably, the paper point used for the sampling step is capable of absorbing fluid and more preferably has a low autofluorescence. The paper point may then be applied to a detection element, again which may be a plate or cuvette (optionally containing a fluid, such as water, or a gel) or may be a device configured to receive a paper point and which is configured for applying the detection step thereto. Care must be taken not to contaminate the paper point after it has been removed from the cavity. Preferably, a paper point sample is taken from each root, thus four measurements may be taken.

As with the first main embodiment, the volume of indicator solution used is determined by endodontic cavity volume—e.g. from 0.1 μl to 2 ml, preferably 500 μl to 2 ml.

Optionally, in one embodiment, only a component of the indicator is incubated in situ in the endodontic cavity. The second (indicating) component, according to a particular embodiment in which the indicator is a two component indicator, may be provided externally to the detection element (e.g. by applying it before, during or after applying the endodontic sample), which is optionally pre-coated with the second component or optionally, the second component may be impregnated into the paper point used to draw the sample from the endodontic cavity, such that the presence of a first component in its active form causes the second component impregnated into the paper point to become fluorescent upon sampling. Accordingly, there is optionally provided according to a further aspect of the invention, a paper point comprising a component of an indicator coated and/or impregnated into at least a portion thereof.

An apparatus according to one embodiment for use with a second main embodiment of the method of the invention comprises a detection unit which is configured to detect the indicator parameter to produce an indication result (or data from which an indication result can be determined) and to display, communicate or transmit the data or indication result and arranged in association with (e.g. mounted on) or coupled with the detection unit a detection element for receiving the endodontic sample (e.g. on a paper point) and on which the detection step may be carried out.

In a preferred embodiment, in which the method utilizes a luminescence-mediated, preferably fluorescence mediated, dye indicator, the detection unit comprises an emission source for providing an excitation signal for (i.e. at a wavelength of absorption of) the active form of the dye. The emission source may be, for example, a bandpass monochromatic source such as LED or laser. Preferably, for an indicator such as Calcein AM, the emission source is configured to emit at 485-500 nm more preferably (but not exclusively) ~488 nm. The detection unit should also be configured to detect light at a wavelength of emission from the dye indicator utilized, and may comprise, for example a photocell or spectrometric device, typically picking up the light emitted after filtering excitation and subsequent emission wavelengths.

Optionally, the apparatus is provided with a fibre optic core (and may be the same apparatus as used in connection with the first main embodiment discussed above only associated with a detection element. In that case, the fibre optic core (detection probe) may be as described above.

Preferably, the emission source (which provides excitation light at approximately the absorbance maximum of the selected detector dye) comprises an LED. The detector unit is typically provided with a dichroic filter to remove the excitation light prior to detection. The final detection step by the detection unit can be done by either a spectrometer or a photo-multiplier-tube or photocell-type detector. For a single dye system, a photo-multiplier tube is the easiest and most cost effective way, but for a multi dye system, a low cost spectrometer will allow multiple signals to be detected.

In a third main embodiment, the incubating step is conducted ex vivo by incubating the viable cell indicator or component thereof with an endodontic sample taken from the endodontic cavity and the measuring and/or detecting step is conducted ex vivo.

Preferably according to this embodiment, the viable cell indicator is luminescence mediated, more preferably fluorescence mediated and more preferably the viable cell indicator comprises a fluorescent dye which has a first form, in the absence of a viable cell population in which the dye is not fluorescent and a second form, in the presence of a viable cell population in which the dye is fluorescent. The transition from the first form to a second form is preferably by way of cleavage of a moiety from the first form of the dye which cleavage is preferably catalysed by a viable cell enzyme.

The indicator preferably comprises one or more fluorescent dye, such as those listed above, but is more preferably a vital dye. Most preferably the indicator is selected from one or more of indocyanine green, sodium fluorescein, carboxyfluorescein, calcein, methylene blue and ProSense 750. In a particularly preferred embodiment, the indicator is calcein (and preferably in its first, non-fluorescent precursor form, calcein-AM).

As mentioned above, the incubating step is conducted ex vivo and so there is required to take a sample of endodontic material from the endodontic cavity. Such a sampling step taken prior to incubation of a sample with an endodontic material may comprise drawing a sample from the endodontic cavity using a syringe or other fluid sampler (in which case it will typically be necessary to first apply a carrier fluid into the endodontic cavity) or using a paperpoint (in which case a carrier fluid applied into the endodontic cavity is optional, otherwise the paper point may be used to sample material from within the cavity physically). The endodontic sample taken may then be applied to an incubating/detection element, which may be, for example, a plate (e.g. microplate), cuvette or other vessel, where the incubation and, optionally, detection step may take place. Preferably, the sampling step comprises absorbing fluid from the endodontic cavity into a paper point (preferably sterile paper point) immersed therein. Paper points are commonly used in dentistry. Preferably, the paper point used for the sampling step is capable of absorbing fluid. The paper point may then be applied to a cuvette or other vessel where it may be incubated with the endodontic sample.

Optionally, the indicator is pre-applied to the indicator element, applied before, during or after the provision of the endodontic sample, or in one option, impregnated into the paper point itself. In the last option, the paper point impregnated with a known amount of indicator may be used to draw up an endodontic sample from the endodontic cavity and then may be immersed in (e.g. a saline solution) in a cuvette and incubated there. The indicator should be incubated for a predetermined period, which is preferably 15 minute or less, more preferably 10 minutes or less, still more preferably 5 minutes or less and most preferably for 2 minutes or less.

The detection step may then be conducted after the incubation period has ended in a similar manner to that described in connection with the second main embodiment above.

The amount of indicator solution required for ex vivo incubation may be a very small volume with well defined concentration since it is not limited by the volume of the endodontic cavity.

In ex vivo detection, there is a lot less physical demand on the apparatus—it can be more complex and in any case doesn't need to have a detection probe.

In a further aspect of the invention, there is provided a paper point for use in endodontic sampling, the paper point comprising an indicator or a component of an indicator, which indicator may be as defined herein, which indicator may optionally be coated onto and/or impregnated into and/or contained within the paper point. The paper point according to this aspect may be made of any suitable material, which is capable of absorbing aqueous fluid, such as paper, composite materials, absorbent polymer forms. Preferably the material of the paper point is filled with a porous filler such as is known in the art, e.g. silica or alumina fillers. Optionally, the indicator or component thereof is contained within, impregnated into or coated onto the paper point. This may be achieved for example by providing the indicator into the material of the paper point prior to rolling, or by coating the paper point material prior to rolling or forming the material into the shape of the paper point. The paper points are preferably provided in the range of sizes of conventional dental paper points.

In a further aspect of the invention, there is provided a method of endodontic therapy for the treatment or prevention of dental abscess, the method comprising, in a patient having or at risk of dental abscess, the steps of: making an opening into a tooth through the crown of the tooth into a pulp chamber; an excavation step comprising excavating pulp from the root of the tooth to expose an endodontic cavity; a cleansing step; a first filling step comprising filling the root(s) of the tooth; and a filling step comprising filling the crown of the tooth, the method being characterized in that after a cleansing step and prior to the first filling step, there is undertaken a viable cell detection step which may indicate the presence of viable cells above a pre-determined threshold, and in that the cleansing step and viable cells detection step are repeated until a viable cell detection step does not indicate the presence of viable cells above a pre-determined threshold.

The viable cell detection step is preferably any method of detecting the presence of viable cells in an endodontic sample as described herein, which method comprises the steps of: incubating a viable cell indicator with an endodontic sample for a pre-determined period; and measuring and/or detecting a change in a parameter associated with the viable cell indicator to obtain an indication result; whereby an indication result representing a pre-determined change in the parameter is indicative of viable cells in the sample.

The indicator for use in this step may be any indicator as described hereinbefore, but is preferably luminescence-mediated, e.g. fluorescence mediated, and most preferably is Calcein AM.

The cleansing step in the method referred to above may include any actions taken on the tooth to cleanse the interior of the tooth and more particularly the endodontic cavity of the root. For example, the cleansing step may comprise one or more of filing to remove residual cellular material and to shape the root to remove minor crevices which may contain viable cells, applying a substance or solution of a substance for killing viable cells (e.g. calcium hydroxide, sodium hypochlorite, chlorhexidine gluconate, ethylenediaminetetraacetic acid, framycetin sulfate) or a formulation for killing viable cells (e.g. Biopure MTAD™ which comprise a mixture of citric acid, docycline and Tween-80) and rinsing the endodontic cavity. In one typical embodiment the cleansing step comprising flushing the endodontic cavity with a solution of sodium hypochlorite, typically in a 4 to 10% aqueous solution, followed by rinsing the endodontic cavity with an aqueous rinse such as water, saline or buffered solution. In any case, it is preferred that the endodontic cavity is rinsed prior to viable cell detection step.

By determining the end-point of cleansing, the endodontic surgeon can: i) be sure that viable cells (especially bacteria) have been eliminated from the endodontic cavity and thereby substantially reduce the risk of re-infection) and ii) minimize the amount of cleansing undertaken. Endodontists typically over-treat at this cleansing stage as there is no chair-side test for determining the end point of cleansing and/or treatment.

In a yet further aspect of the invention, there is provided an indicator for use in a method of endodontic therapy, such as that method described above. Preferably, the indicator is for detecting the therapeutic endpoint for a bacteriocidal or cleansing step of the method and/or for use in a viable cells detection step of the method.

The indicator according to this aspect may be any suitable indicator as described herein. Preferably, the indicator is luminescence-mediated (e.g. fluorescence-mediated) and may, for example, be selected from one or a combination of (compounds following which are referred to in either their active, i.e. fluorescent, form or their quenched, i.e. non-fluorescent, form): DAPI, EBFP, Hoechst 33258 dye, 7-hydroxy-4-methylcoumarin, Quinine Sulfate, 4-methylumbelliferone, 5-FAM, Calcein, DiO, Fluorescein, FLUO-3, FLUO-4, EGFP, GFP, Oregon Green 514, Rhodamine Green, SYBR Gold, SYBR Green, SYTO 9, SYTOX Green, YFP, LIVE/DEAD BacLight, AlExa Fluor 555, Cy3, Ethidium Bromide, Ethidium Homodimer-1, Propidium Iodide, Resorufin, RFP, Rhod-2, Rhodamine Red, SYTOX Orange, TAMRA, Texas Red, TRITC, Allophycocyanin, Cy5, DRAQ5, SYTOX Red, Indocyanine green, sodium fluorescein, carboxyfluorescein, methylene blue, or ProSense 750.

Where an active (fluorescent) form of the indicator is mentioned above, it is to be understood that the indicator comprises an inactive probe form thereof convertible to the active form in the presence of viable cells. In many examples, such as Calcein as the active form indicator, the indicator will require a precursor form such as Calcein-AM or the active form may be quenched in a peptide, such as 5FAM-peptide-TAMRA, whereby viable cell enzyme mediated cleavage will release the active fluorophore thus indicating presence of viable cells.

Preferably, the indicator is a vital dye.

Preferred examples of indicator (in active form) are indocyanine green, sodium fluorescein, carboxyfluorescein, calcein, methylene blue and ProSense 750.

In a particularly preferred embodiment, the indicator is calcein-AM.

The indicator according to this aspect may be provided in a suitable amount to elicit the indicative effect (which may depend on whether the indicator is applied in vivo, where there may be greater background fluorescence, or ex vivo). Optionally, the indicator is provided in an ampoule pre-loaded with a solution of the indicator in a desired amount and concentration, which amount should be sufficient to treat an endodontic cavity (and is proposed above). Alternatively, the indicator may provided in a specified amount impregnated into a paper point for sampling an endodontic sample. Preferably, in the case of preferred indicators, such as calcein AM, the indicator is provided in an ampoule or pre-loaded syringe as an aqueous solution in an amount in the range from 10 µl to 500 µl and in a concentration in the range from 10 µM to 1 mM.

In a yet further aspect of the invention, there is provided a method of cleansing an endodontic cavity during endodontic therapy, the method comprising conducting a one or a plurality of cleansing steps as defined above, and between each cleansing step conducting an end-point determination step (being a cell detection step, preferably viable cell detection step) until such end-point determination step indicates an end point (being a point at which viable cell population or indication thereof is not above a certain pre-determined value).

In another aspect, there is provided a method of diagnosis of endodontic infection on the human or animal body, the method comprising the steps of incubating a bacterial cell indicator with an endodontic sample for a pre-determined period; and measuring and/or detecting a change in a parameter associated with the bacterial cell indicator to obtain an indication result; whereby an indication result representing a pre-determined change in the parameter is indicative of bacterial cells in the sample.

The indicator, preferably viable cell activatable quenched fluorescent dye, is useful in endodontic imaging.

There is provided in a further aspect of the invention, use of an indicator, e.g. a fluorescent dye, for detecting viable cells in an endodontic material (fluid/tissue) sample by incubating the indicator with a sample of endodontic material taken from a patient and undertaking a detection step for detecting a parameter of the indicator indicative of viable cell presence in the sample.

In another, more general, aspect, there is provided a method of detecting the presence of cells or cellular material in an endodontic sample, the method comprising the steps of: incubating a cell indicator with an endodontic sample for a pre-determined period; and measuring and/or detecting a change in a parameter or set of parameters associated with the cell indicator to obtain an indication result, whereby an indication result representing a pre-determined change in the parameter is indicative of cells or cellular material in the sample.

Embodiments and features of the method and apparatus described herein with respect to other aspects, and in particular the aspects of the invention associated with viable cell detection above, apply and are incorporated as embodiments of this broader aspect where the context allows by substituting limitation to viable cells or viable cell material with cells or cell material. For example, embodiments of the methods described above with reference to detecting the presence of viable cells or cellular material are incorporated here as detecting the presence of cells or cellular material; and embodiments described with reference to viable cell indicator are incorporated here as cell indicator (which may be considered an indicator which indicates the presence of a cell or cell-indicative material and can distinguish over the absence of cells or cell-indicative material and optionally can represent a quantity of cell or cell-indicative material), where the context allows.

According to this method, and the three main embodiments (described above with reference to viable cell detection methods) generalized to refer to this method, cells may be viable or non-viable (live or dead) cells and cellular material includes intracellular components and extracellular materials that are excreted by or up-regulated in the presence of cells. Cellular material includes, for example structures or compounds associated with or derived from cells, e.g. extracellular such structures or compounds, such as constituent polysaccharides and enzymes which may form or be comprised within a biofilm.

Among cell indicators according to this aspect are those types of and particular indicators described above with reference to viable cell detection which may be generalised to indicate the presence of cells or cell material. The indicator may be a global indicator (e.g. global dye or stain) capable of identifying, but not discriminating, viable and non-viable cells or may be an indicator which can identify and discriminate viable cells and/or identify and discriminate dead or non-viable cells. Preferably, the cells according to this aspect are potentially functioning cells, viable components of cells or cellular material, recently dead cells or viable cells and most preferably viable cells (in accordance with the main aspect of the present invention).

The invention will now be described in more detail, without limitation, with reference to the accompanying Figures.

In FIG. 1, there is a schematic flow-type diagram by which one embodiment of the invention is shown to be implemented according to the three main embodiments of the method of the invention. According to FIG. 1, three embodiments, A, B and C, of a sampling and detecting step 1 of in each case a tooth 3 having an endodontic cavity 5 formed therein containing bacterial populations 7. A fluorescent indicator dye is provided in the form of an indicator solution 9 in each method A, B and C. In methods A and B, the indicator solution 9 is provided in the endodontic cavity 5 where it is incubated with the sample, whereas in method C, the indicator solution 9 is provided to an incubating vessel in the form of cuvette 11. In method A of the sampling and detecting step 1, the indicator solution 9 is added to the endodontic cavity 5 to incubate as an endodontic sample therein for a pre-determined period (e.g. 10 minutes or less, optionally 2 minutes or less), then a detection probe 13 in the form of a fibre optic core having a disposable tip is immersed into the indicator solution 9 in the endodontic cavity 5 to detect fluorescence in any activated indicator (representing the presence of bacterial populations 7). The detection probe 13 is coupled with detector 15 via dichroic filter 17. The detector 15 comprises, coupled with the dichroic filter 17 an excitation unit 19 consisting of an LED light source 21 and an excitation filter 23, and a detection unit 25 comprising a photodetector 27 which feeds data to a microprocessor 29 for analysis and displays information via a user display 31. Thus according to method A, an excitation signal is transmitted through the dichroic filter 17 through the detection probe 13 into the sample within the endodontic cavity 5. Any indicator that has been activated by contact with live bacterial cells 7 absorbs the excitation signal and emits a fluorescent emission signal, which is collected by the detection probe, passes through the dichroic filter 17 and is detected by the detection unit 25 confirming the presence of bacterial cell populations. In method B, indicator solution 9 is again provided to the endodontic cavity 5 and allowed to incubate there for the pre-determined period. Then a sample is taken from the endodontic cavity by use of an absorbent paper point 33. This absorbent paper point 33 carrying any cell populations or indicator activated by cell populations is presented for detection before the detector. The detection step is carried out in the same way as for method A, only optionally absent the detection probe 13 and instead using a detection element (not shown). In method C, indicator solution 9 is not applied to the endodontic cavity 5. Instead, an absorbent paper point 35 is used to obtain a sample of endodontic material, including any bacterial cell population 7, from the endodontic cavity 5. This paper point 35 may then be placed into a cuvette 11 containing indicator solution 9 and incubated there for a pre-determined period. Then, the cuvette 11 may be presented to the detector and the detection step carried out on the cuvette 11 and its contents in a similar manner to method A in order to determine the presence or absence of cell populations in the endodontic sample.

EXAMPLE

Example 1

Processing of Extracted Teeth

Twenty freshly extracted, single rooted teeth were obtained under ethical Approval (South East London ethical approval 10/H0804/056). Each tooth had the crown removed to obtain 15 mm long specimens, using a 0.3 mm thickness diamond wafering blade (Extec, Enfield, Conn., USA) on a 11-1180 Isomet low speed saw (Buehler, Düsseldorf, Germany). Root canal patency was confirmed using an ISO 10 K-file. Canals were instrumented with Gates Glidden (nr. 2-4) for coronal flaring followed by ProTaper F3 instrumentation and apical instrumentation with an ISO 45 K-file 1 mm short of the working length. Irrigation throughout the instrumentation was undertaken with sterile saline. Each root was then sectioned longitudinally through the root canal using the low speed saw. The specimen's halves were then reapproximated and placed in a block of freshly mixed impression material (Aquasil™ Hard Putty/Fast Set, Dentsply) contained in 5 ml bijou vials with the coronal portion of the root flush with the bottle opening. After setting, the root halves were immersed in 15% EDTA for 1 min to remove the smear layer and copiously rinsed with saline. Specimens were then sterilised in an autoclave at 134° C. for 10 min.

Establishment of In Vitro Biofilm Model

Multispecies mature biofilm from clinical isolates, identified through sequencing (*Actinomyces radicidentis*,

*Enterococcus faecalis, Propionibacterium acnes, Streptococcus epidermidis, Streptococcus oxalis*) were grown in 24 multiwell plates for two weeks on root halves using a modification of the established 5-day biofilm protocol (Gmür & Guggenheim 1983). Briefly, the strains were routinely cultured anaerobically at 37° C. on Fastidious Anaerobe Agar (LabM) supplemented with 5% defibrinated horse blood. Starter cultures were set up in filter-sterilized modified fluid universal medium incubated anaerobically at 37° C. for 3 h, until the growth appeared moderately turbid. The turbidity was adjusted with fresh mFUM to OD at 540 nm (Labsystems iEMS Reader MF) to 0.5. Each root was incubated with 1.5 ml of the multispecies biofilm culture in 24 well trays and the medium was replaced daily for the first seven days. Following biofilm growth the root halves were re-assembled in the silicon block. Subsequently, the specimens were randomly allotted to the experimental groups to test the microendoscopic visualization of biofilms.

Experimental Groups:
1. Group A) 1% NaOCl solution irrigation (5 ml)
2. Group B) Saline irrigation (5 ml)
3. Group C) Control—no irrigation In all groups, microendoscopy observations were carried out at baseline before applying the treatment: firstly samples were incubated for 10 minutes with Calcein AM. Observation of specimens from Group A) and B) was repeated after irrigation (after the same time required for irrigation in group C). In Group A) the dye was reapplied for 10 minutes after D/E Neutralizing Broth (BD DIFCO, Franklin Lakes, N.J. USA) (2 ml) to prevent bleaching of the stain. Following the observations, the root halves were fixed with glutaraldehyde and SEM imaging undertaken to confirm presence or elimination of the biofilm.

Microendoscopy

For the microendoscopic observation, 50 µl of 100 nM calcein acetoxymethyl ester (Fluka Analytical, Gillingham, UK) were injected into the root canal space and incubated at room temperature for 10 min. Imaging was carried out using a prototype Cellvizio-GI confocal microendoscope (Mauna Kea Technologies, Paris France), fitted with a 300 µm mini-O fibre-optic probe. The probe was adjusted by de-sheathing 20 mm to enable root canal space access. The root canals were examined using the 488 nm laser excitation source with fluorescence emission discrimination from reflection components using a 515 nm long pass emission filtration prior to image detection at a frame rate of 12 images/sec. Images of 250 µm field diameter were obtained with the 300 µm fibre. Images for each specimen were obtained at standard depths of the root canal space (−2 mm, −8 mm, −14 mm) and exported with proprietary software (Mauna Kea Technologies). Fluorescence controls were prepared from pure biofilms and dentine specimen with and without (autofluorescence background determination) Calcein AM. Representative images for each sample type, probe depth and probe diameter were obtained using the CellVizio software package (Mauna Kea Technologies). Fluorescence controls were prepared from native pulp cells incubated in Calcein AM.

Bacterial Sampling and Quantification

After each root had been subjected to its respective irrigation protocol and imaging steps, the root halves were aseptically placed in a 9 cm petri dish (SLS, East Riding of Yorkshire, UK). Two sterile paper points (Dentsply, Maillefer) were used for each root half to sample the root canal to quantify the viable counts. The sampled biofilm was dispersed by thorough vortexing with sterile glass beads. Serial dilutions were prepared in 0.9 ml aliquots of BHI (Brain-Heart infusion Broth-Lab M, UK) and 0.1 ml aliquots were plated onto duplicate FAA plates. Plates were incubated anaerobically for 7 days. After the incubation, the numbers of colonies on FAA plates were counted. The statistical analysis was performed in SPSSPC (Ver 18.0) using a single factor: ANOVA to compare the quantitative viable counts between the three experimental groups.

Spectrophotometric Analysis

A spectrophotometric approach has been devised to quantify the fluorescence of viable bacteria present in the root canal space pre and post treatment. An experimental set up consisting of an LED light source a dichroic mirror and a beam splitter was coupled with a 200 µm single fibre optic cable de-sheathed in its extremity. The dichroic mirror beam splitter was connected to a spectrophotometer linked via USB to a laptop to record the spectra curves.

Paper Point Spectrophotometric and Microendoscopic Analysis

The aforementioned microendoscopic and spectrophotometric technique have been tested also in an indirect fashion by mean of paper point sampling.

Sterile paper points (PTU, Size F2, Dentsply) were inserted in the canals after the irrigation regimens described before and the neutralization step. The sampling was conducted by scrubbing the paper point along the root canal walls for the whole working length. Paper points were then incubated for 10 minutes in 200 µl of 100 nM calcein acetoxymethyl ester (Fluka) placed in 24 multiwell plates.

After staining of the recovered bacteria microendoscopy was completed as previously described observing the fluorescent cells for the whole length of the paper point. After incubation paper points were also analysed with the spectrophotometric fibre to quantify the emitted fluorescence, recording the peak on the length of point. Non incubated paper points and non-sampled incubated paper point were imaged to determine background and autofluorescence.

Results

MKT Probe Direct Visualisation

Figure 2:
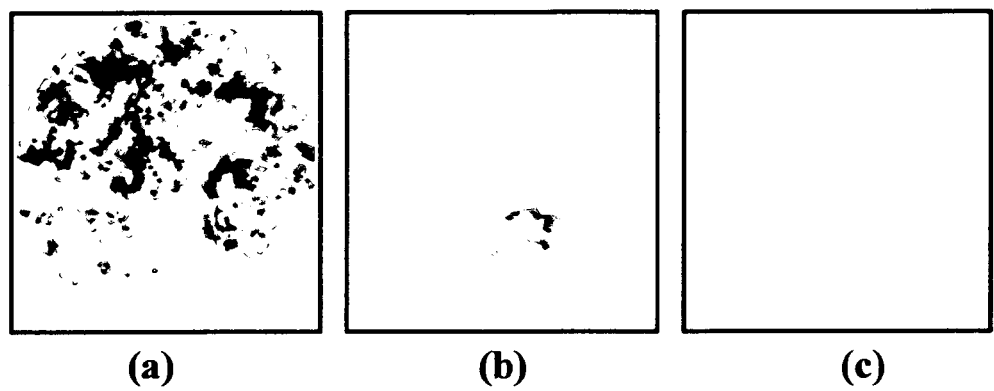
FIG. 2 a-c shows single point confocal fluorescent microendoscopic images 1 mm from a root apex after incubation of the root with calcein-AM indicator prior to (FIG. 2a) and after (FIGS. 2b and 2c) sequences of irrigation with sodium hypochlorite.

FIG. 2 shows an example of the apical part of the root canal at different stages of the root canal treatment: clusters of bacteria approximately 5 µm in diameter are visible. When applied to extracted teeth, excellent intra-canal imaging throughout the entire root canal was obtained using a 300 µm microendoscopy probe. It was possible to quantify and analyse the emitted fluorescence of the bacteria infecting the root canal space. Whilst the method was applicable for re-examination, the clinical endpoint can easily be determined by the absence of a detectable fluorescent signal, as seen in FIG. 2.

Microbial Quantification

Table 1 shows the viable post-experimental counts of the multi-species biofilms. The biofilms were grown in triplicates, plated and incubated anaerobically on FAA plates for seven days. The values are given as log 10 of the average of triplicate counts±S.D. The value of the bacterial counts was significantly lower for group A) compared with Group B) and C).

Spectrophotometric Analysis and Microbial Quantification Comparison

Figure 3:
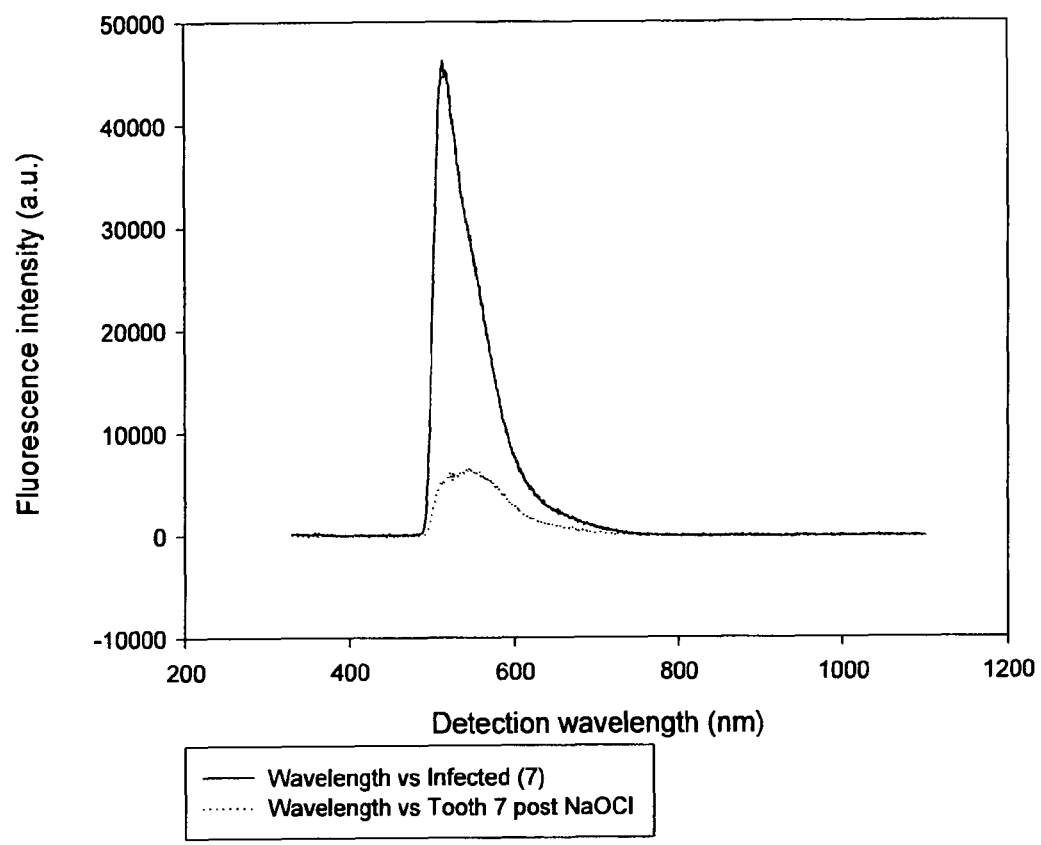
FIG. 3 shows a graph of fluorescence against wavelength for spectrophotometric readings pre and post irrigation with 1% NaOCl solution in one group of examples in accordance with the invention.
Figure 4:
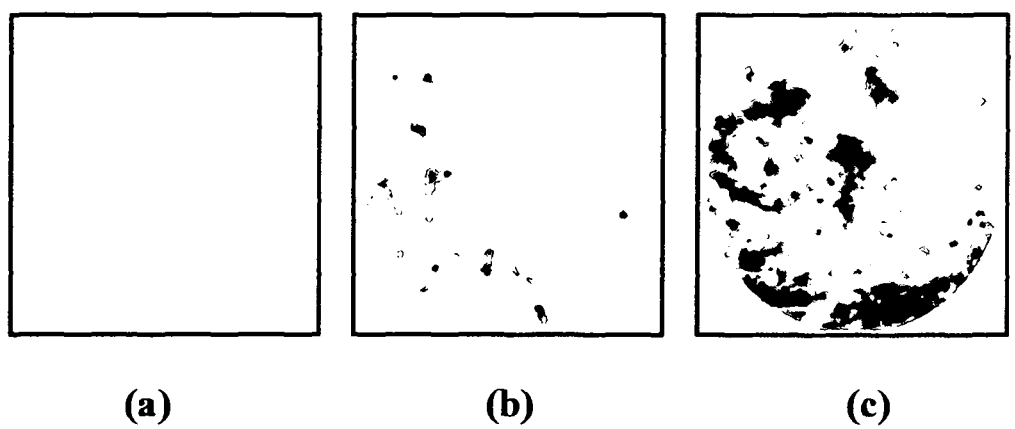
FIG. 4 a-c shows confocal fluorescent microendoscopic images of a paper point imaged for background fluorescence (FIG. 4a), after repeated irrigation with sodium hypochlorite (FIG. 4b), and observed after post-sampling staining (FIG. 4c).

FIG. 3 shows the graph of the spectrophotometric reading pre and post irrigation with 1% NaOCl solution in Group A). The ideal endodontic endpoint would be represented by the zero reading of the spectrophotometer with no viable fluorescent bacterial cell detected Paper Point Spectrophotometric and Microendoscopic Analysis Similar results were obtained with an indirect paper point approach. The sensitivity of the system was comparable to the direct approaches. The autofluorescence of the paper point was negligible and the collected viable biofilm was visible and could be quantified by spectrophotometer (FIG. 4).

TABLE 1

Microbial counts expressed as $\log_{10}$ for the three treatment groups after anaerobic growth.

| Treatment Groups | $\text{Log}_{10}$ (Mean ± SE) |
|---|---|
| (A) Sodium hypochlorite | 0.51* |
|  | (0.01) |
| (B) Saline Irrigation | 6.43 |
|  | (0.02) |
| (C) No irrigation (Control) | 7.96 |
|  | (0.04) |

*Value significantly lower compared with Group (B) and (C)

The invention has been described with reference to a preferred embodiment. However, it will be appreciated that variations and modifications can be effected by a person of ordinary skill in the art without departing from the scope of the invention.

The invention claimed is:

1. A method of detecting a presence of viable cells in an endodontic sample, the method comprising:
    contacting a viable cell indicator with an endodontic sample; and
    measuring and/or detecting a change in a parameter associated with the viable cell indicator to obtain an indication result;
    wherein an indication result representing a pre-determined change in the parameter is indicative of viable cells in the sample; and
    wherein the indication result is obtained without cell culture of the sample.

2. The method according to claim 1, wherein:
    A) the step of contacting the viable cell indicator with the endodontic sample is conducted within the endodontic cavity by applying a viable cell indicator to the endodontic cavity and the measuring and/or detecting step is conducted in the endodontic cavity; or
    B) the step of contacting the viable cell indicator with the endodontic sample is conducted within the endodontic cavity by applying a viable cell indicator to the endodontic cavity and the measuring and/or detecting step is conducted ex vivo; or
    C) the step of contacting the viable cell indicator with the endodontic sample is conducted ex vivo by contacting the viable cell indicator with an endodontic sample taken from the endodontic cavity and the measuring and/or detecting step is conducted ex vivo.

3. The method according to claim 2, wherein the step of contacting the viable cell indicator with the endodontic sample is conducted within the endodontic cavity by applying a viable cell indicator to the endodontic cavity and the measuring and/or detecting step is conducted in the endodontic cavity, and
    further wherein the measuring and/or detecting step comprises inserting a detection probe into the endodontic cavity and (i) detecting a parameter associated with the viable cell indicator or (ii) transmitting data relating to a parameter associated with the viable cell indicator to a detector in order to arrive at the indication result.

4. The method according to claim 2 wherein the step of contacting the viable cell indicator with the endodontic sample is conducted within the endodontic cavity by applying a viable cell indicator to the endodontic cavity and the measuring and/or detecting step is conducted ex vivo, and
    wherein the method further comprises:
        after contacting of the viable cell indicator with the endodontic sample in the endodontic cavity, extracting at least a portion of the contacted sample from the endodontic cavity; and
        subjecting the extracted portion to measurement and/or detection of the parameter associated with the viable cell indicator on a suitable substrate or in a suitable vessel to obtain the indication result.

5. The method according to claim 4, wherein the step of extracting at least a portion of the contacted sample from the endodontic cavity is achieved using an absorbent paper point and the substrate is the absorbent paper point.

6. The method according to claim 2, wherein the step of contacting the viable cell indicator with the endodontic sample is conducted ex vivo by contacting the viable cell indicator with an endodontic sample taken from the endodontic cavity and the measuring and/or detecting step is conducted ex vivo, and
    wherein the method further comprises:
        sampling, scraping or cleaning the endodontic cavity with an absorbent paper point in order to take an endodontic sample for contact with the viable cell indicator; and
        contacting said endodontic sample with the viable cell indicator by soaking the paper point in a solution of the viable cell indicator.

7. The method according to claim 1, wherein the method is luminescence mediated.

8. The method according to claim 1, wherein the viable cell indicator is a luminescence mediated indicator, the parameter associated with the viable cell indicator is luminescence and the measurement and/or detection step is a luminescence measurement and/or detection step.

9. The method according to claim 8, wherein the viable cell indicator has a first form in the absence of viable cells which displays a first luminescence behavior and a second form in the presence of viable cells which displays a second luminescence behavior.

10. The method according to claim 8, wherein the luminescence is fluorescence.

11. The method according to claim 10, wherein:
    the indicator comprises a fluorescent dye which has an inactive form in the absence of viable cells which inactive form is not fluorescent, and which has an active form in the presence of viable cells which active form is fluorescent, and
    a detection and/or measurement step may detect fluorescence in a sample to arrive at the indication result.

12. The method according to claim 11, wherein the fluorescence measurement step is carried out using fluorescence microendoscopy.

13. The method according to claim 11, wherein the dye is contacted with the endodontic sample for a period of up to 10 minutes.

14. The method according to claim 1, wherein the indicator is selected from the group consisting of indocyanine green, sodium fluorescein, carboxyfluorescein, calcein, methylene blue, protease activatable fluorescent agents, and combinations thereof.

15. The method according to claim 1, wherein the indicator is calcein-AM.

* * * * *